US010207926B2

(12) United States Patent
Naito et al.

(10) Patent No.: US 10,207,926 B2
(45) Date of Patent: Feb. 19, 2019

(54) OZONE GENERATOR

(71) Applicant: Ushio Denki Kabushiki Kaisha, Tokyo (JP)

(72) Inventors: Keisuke Naito, Tokyo (JP); Nobuyuki Hishinuma, Tokyo (JP); Shinji Suzuki, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/754,129

(22) PCT Filed: Aug. 8, 2016

(86) PCT No.: PCT/JP2016/073313
§ 371 (c)(1),
(2) Date: Feb. 21, 2018

(87) PCT Pub. No.: WO2017/033727
PCT Pub. Date: Mar. 2, 2017

(65) Prior Publication Data
US 2018/0230011 A1  Aug. 16, 2018

(30) Foreign Application Priority Data
Aug. 26, 2015  (JP) .................. 2015-166984

(51) Int. Cl.
*A61L 9/00* (2006.01)
*C01B 13/10* (2006.01)
(Continued)

(52) U.S. Cl.
CPC .............. *C01B 13/10* (2013.01); *A61L 2/202* (2013.01); *A61L 2/26* (2013.01); *A61L 9/046* (2013.01); *A61L 9/12* (2013.01); *C01B 13/11* (2013.01)

(58) Field of Classification Search
CPC ..... A61L 2/24; A61L 2/14; A61L 2/08; A61L 2/18; A61L 2/10; A23L 3/28
(Continued)

(56) References Cited

U.S. PATENT DOCUMENTS

2004/0120850 A1* 6/2004 Kaiser ...................... A61L 2/10
422/22

FOREIGN PATENT DOCUMENTS

JP    2002-166270 A    6/2002
JP    2003-040607 A    2/2003
(Continued)

OTHER PUBLICATIONS

Kogelschatz; Silent discharges for the generation of ultraviolet and vacuum ultraviolet excimer radiation; Pure & Appl. Chem.; vol. 62, No. 9; 1990; pp. 1667-1674.
(Continued)

*Primary Examiner* — Monzer R Chorbaji
(74) *Attorney, Agent, or Firm* — Studebaker & Brackett PC

(57) ABSTRACT

The present invention has as its object the provision of an ozone generator that can generate ozone with high efficiency. The ozone generator of the present invention includes: source gas supply means for supplying a source gas containing oxygen; a gas flow channel forming member for forming a gas flow channel through which the source gas from the source gas supply means flows; and an ultraviolet light source for emitting ultraviolet light, the ultraviolet light source being disposed in the gas flow channel. The ozone generator irradiates the source gas flowing through the gas flow channel with the ultraviolet light from the ultraviolet light source to cause the oxygen in the source gas to absorb the ultraviolet light and thereby generate ozone. The ultraviolet light source comprises an excimer lamp for emitting
(Continued)

ultraviolet light with a wavelength of not more than 200 nm. A flow rate of the source gas in a region where the ultraviolet light source is disposed in the gas flow channel is not lower than 0.1 m/s.

6 Claims, 6 Drawing Sheets

(51) Int. Cl.
- *C01B 13/11* (2006.01)
- *A61L 2/20* (2006.01)
- *A61L 2/26* (2006.01)
- *A61L 9/04* (2006.01)
- *A61L 9/12* (2006.01)

(58) Field of Classification Search
USPC .......................................... 422/34, 28, 305
See application file for complete search history.

(56) References Cited

FOREIGN PATENT DOCUMENTS

| | | |
|---|---|---|
| JP | 2003-165711 A | 6/2003 |
| JP | 2006-096600 A | 4/2006 |
| JP | 2009-057279 A | 3/2009 |

OTHER PUBLICATIONS

International Search Report issued in PCT/JP2016/073313; dated Sep. 27, 2016.

An Office Action; "Decision to Grant a Patent" issued by the Japanese Patent Office on Dec. 6, 2016, which corresponds to Japanese Patent Application No. 2015-166984.

* cited by examiner

OZONE GENERATOR

TECHNICAL FIELD

The present invention relates to an ozone generator, and, more specifically, to an ozone generator configured to irradiate a source gas containing oxygen with ultraviolet light.

BACKGROUND ART

Ozone having strong oxidation power has been conventionally used in various fields for the purpose of, for example, sterilization, deodorization, decolorization, removal of organic substances, removal of hazardous substances, and synthesis of chemical substances.

A photochemical reaction method using ultraviolet light, for example, has been known as one of methods for industrially generating ozone ($O_3$). In this photochemical reaction method, a source gas containing oxygen ($O_2$) is irradiated with ultraviolet light emitted from an ultraviolet light source such as an ultraviolet lamp including a discharge space in an arc tube. This causes the oxygen in the source gas to absorb the ultraviolet light, thereby causing an ozone generating reaction to generate ozone. Advantageously in such a photochemical reaction method, no nitrogen oxide ($NO_x$) as in a silent discharge method, for example, is generated even when a gas containing oxygen and nitrogen is used as a source gas. Moreover, since discharge occurs only in the discharge space in the arc tube, no dust attributable to an electrode is mixed into an ozone-containing gas containing the generated ozone.

In the photochemical reaction method, a low-pressure mercury lamp is generally employed as an ultraviolet light source (see Patent Literature 1, for example).

Patent Literature 1 discloses an ozone generator having a configuration in which a rod-shaped low-pressure mercury lamp is disposed inside a gas flow channel forming member through which a source gas containing oxygen flows, i.e., in a gas flow channel.

The ozone generator that employs the low-pressure mercury lamp as an ultraviolet light source, however, has the following problem.

Typical wavelengths of light emitted from the low-pressure mercury lamp are 185 nm and 254 nm. The wavelength of 185 nm is an ozone generating wavelength, whereas the wavelength of 254 nm is an ozone decomposition wavelength. Thus, when the low-pressure mercury lamp is employed as an ultraviolet light source, an ozone generating reaction and an ozone decomposition reaction occur at the same time. Furthermore, an oxygen atom (O) generated by the ozone decomposition reaction reacts with ozone, thus reducing the amount of ozone. Therefore, no efficient ozone generation can be expected.

To address such a problem, the use of an excimer lamp that emits light containing much ozone generating wavelength as an ultraviolet light source has been proposed in recent years (see Patent Literature 2, for example).

Patent Literature 2 discloses an ozone generator having a configuration in which a gas flow channel forming member made of an ultraviolet transmitting material and having a double-tube structure is disposed so as to surround a rod-shaped excimer lamp. In this ozone generator, a source gas supplied to the gas flow channel forming member is in an isolated state so as not to be in contact with an electrode of the excimer lamp. In this ozone generator, a high-frequency emission excimer lamp with a frequency of 1 MHz to 20 MHz is employed as the excimer lamp, and an ultraviolet reflection member is provided on the outer periphery of the gas flow channel forming member. This ozone generator can air-cool the excimer lamp by flowing a refrigerant such as a nitrogen gas through a gap between the excimer lamp and the gas flow channel forming member.

CITATION LIST

Patent Literature

Patent Literature 1: Japanese Patent Application Laid-Open No. 2003-040607
Patent Literature 2: Japanese Patent Application Laid-Open No. 2003-165711

SUMMARY OF INVENTION

Technical Problem

In the ozone generator that employs the excimer lamp as an ultraviolet light source, however, conditions for efficiently generating ozone are inapparent. More specifically, Patent Literature 2 describes various configurations having different positional relationships between the excimer lamp and a gas flow channel of the source gas formed by the gas flow channel forming member having the double-tube structure as specific configurations of the ozone generator. Patent Literature 2, however, describes nothing about supply conditions of the source gas, i.e., the flow rate of the source gas in the gas flow channel.

In an ozone generator that employs a low-pressure mercury lamp as an ultraviolet light source, for example, in the ozone generator described in Patent Literature 1, on the other hand, it is preferable that the source gas in the gas flow channel has a flow rate of 5 to 50 m/s in a configuration where the low-pressure mercury lamp is disposed inside the gas flow channel forming member (gas flow channel).

Applying the supply conditions (flow rate conditions) of the source gas in the ozone generator that employs the low-pressure mercury lamp to the ozone generator that employs the excimer lamp is unpractical due to the too high flow rate. In the ozone generator that employs the excimer lamp, if the excimer lamp emits no light with an ozone decomposition wavelength, there is no need to promptly discharge ozone generated in the gas flow channel forming member by the flow of the gas.

The present invention has been made in view of the foregoing circumstances and has as its object the provision of an ozone generator that can generate ozone with high efficiency.

Solution to Problem

According to the present invention, there is provided an ozone generator including: source gas supply means for supplying a source gas containing oxygen; a gas flow channel forming member for forming a gas flow channel through which the source gas from the source gas supply means flows; and an ultraviolet light source for emitting ultraviolet light, the ultraviolet light source being disposed in the gas flow channel. The ozone generator irradiates the source gas flowing through the gas flow channel with the ultraviolet light from the ultraviolet light source to cause the oxygen in the source gas to absorb the ultraviolet light and thereby generate ozone.

The ultraviolet light source comprises an excimer lamp for emitting ultraviolet light with a wavelength of not more than 200 nm.

A flow rate of the source gas in a region where the ultraviolet light source is disposed in the gas flow channel is not lower than 0.1 m/s.

In the ozone generator of the present invention, the excimer lamp that constitutes the ultraviolet light source may preferably have a rod shape, and the excimer lamp may preferably be disposed along a gas flowing direction in the gas flow channel.

In the ozone generator of the present invention, the source gas flowing through the gas flow channel may preferably have a relative humidity of not more than 30% RH.

The ozone generator of the present invention may preferably produce an ozone concentration of not more than 50 ppm in an ozone-containing gas discharged to the outside and may preferably be used as a sterilization and deodorization device for residence space.

Advantageous Effects of Invention

In the ozone generator of the present invention, the excimer lamp that emits ultraviolet light with a wavelength of not more than 200 nm is employed as the ultraviolet light source. Thus, light (ultraviolet light) from the ultraviolet light source contains no light with an ozone decomposition wavelength. Thus, no generated ozone is decomposed as a result of being irradiated with light (ultraviolet light) from the ultraviolet light source. Moreover, since the ultraviolet light source is disposed in the gas flow channel and the flow rate of the source gas in the region where the ultraviolet light source is disposed in the gas flow channel is set to be not lower than 0.1 m/s, reduction in ozone yield can be sufficiently suppressed.

Therefore, the ozone generator of the present invention can generate ozone with high efficiency.

DESCRIPTION OF EMBODIMENTS

An embodiment of an ozone generator of the present invention will be described below.

Figure 1:
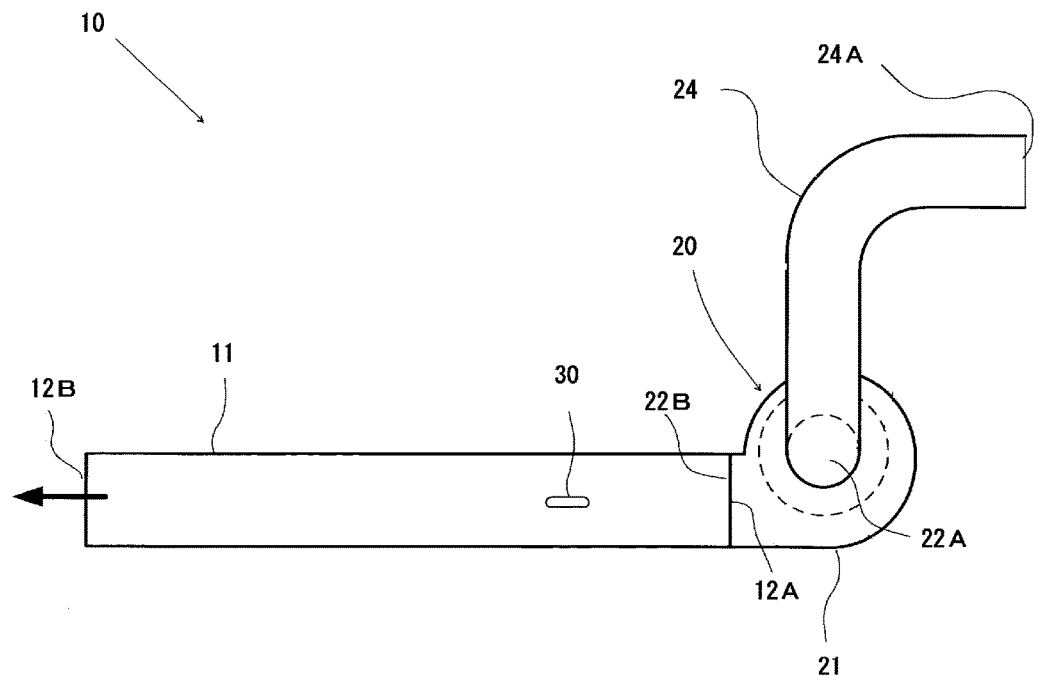
FIG. 1 is an explanatory view illustrating a schematic configuration example of an ozone generator of the present invention.

FIG. 1 is an explanatory view illustrating a schematic configuration example of the ozone generator of the present invention.

The ozone generator 10 irradiates a source gas containing an oxygen with ultraviolet light to cause oxygen in the source gas to absorb the ultraviolet light and thereby generate ozone and discharges an ozone-containing gas containing the generated ozone to the outside.

The ozone generator 10 includes a gas flow channel forming member 11 having a long length and a right cylindrical shape. The gas flow channel forming member 11 has a gas feed port 12A at one end and a gas discharge port 12B at the other end. Source gas supply means 20 is connected to the gas feed port 12A. Inside the gas flow channel forming member 11, an ultraviolet light source comprising an excimer lamp 30 with a circular rod shape is disposed so that the whole emission region is positioned therein. The excimer lamp 30 has an outer diameter smaller than an inner diameter of the gas flow channel forming member 11 and has an emission length (the length of the emission region) smaller than the whole length of the gas flow channel forming member 11. The excimer lamp 30 is supported by a support member (not shown) in the gas flow channel forming member 11 in such a manner that its tube axis (the central axis of the lamp) approximately coincides with the tube axis of the gas flow channel forming member 11. That is, the excimer lamp 30 is provided in such a manner that the outer periphery of the excimer lamp 30 is separated, over the whole circumference thereof, from the inner periphery of the gas flow channel forming member 11 to form a ring-shaped space between the outer periphery of the excimer lamp 30 and the inner periphery of the gas flow channel forming member 11. In this manner, a gas flow channel forming space including the ring-shaped space (specifically, a circular ring-shaped space) and a columnar space (specifically, a cylindrical space) communicated with the ring-shaped space constitutes a gas flow channel through which the source gas supplied from the source gas supply means 20 flows toward the gas discharge port 12B in the gas flow channel forming member 11. That is, the excimer lamp 30 is disposed in the gas flow channel.

In the gas flow channel forming member 11, an ozone generating part that irradiates the source gas with ultraviolet light from the excimer lamp 30 is formed by a region where the emission region of the excimer lamp 30 is present and its neighboring region. A source gas flowing part is provided upstream of the ozone generating part (the gas feed port 12A side), and an ozone-containing gas flowing part is provided downstream of the ozone generating part (the gas discharge port 12B side).

In the example of FIG. 1, the excimer lamp 30 is disposed at a position near the gas feed port 12A in the gas flow channel forming member 11.

In FIG. 1, the flowing direction of the gas in the ozone generator 10 is indicated by the arrow.

The whole inner periphery of the gas flow channel forming member 11 in the ozone generating part and the ozone-containing gas flowing part, i.e., a region of the inner periphery to be in contact with the source gas irradiated with ultraviolet light from the excimer lamp 30 has resistance against ozone.

In the example of FIG. 1, the gas flow channel forming member 11 is formed from a vinyl chloride resin, so that the whole inner periphery has resistance against ozone.

The whole inner periphery of the gas flow channel forming member 11 in the ultraviolet irradiation region, i.e., the ozone generating part preferably has an ultraviolet reflection ability.

The gas flow channel forming member 11 having the ultraviolet reflection ability in the ultraviolet irradiation region can achieve the effective utilization of ultraviolet light from the excimer lamp 30. Thus, ozone can be generated with higher efficiency in the ozone generator 10.

The excimer lamp 30 that constitutes the ultraviolet light source emits ultraviolet light with a wavelength of not more than 200 nm.

The ultraviolet light source constituted by the excimer lamp 30 that emits ultraviolet light with a wavelength of not more than 200 nm can prevent the source gas from being irradiated with ultraviolet light with an ozone decomposition wavelength (specifically, light with a wavelength of 254 nm). Thus, no generated ozone is decomposed as a result of being irradiated with ultraviolet light from the ultraviolet light source. Furthermore, the excimer lamp 30 needs no large input power in order to obtain a large ozone yield as in a low-pressure mercury lamp. Thus, the ozone generator 10 can generate ozone with high efficiency.

The "excimer lamp" as used herein refers to a lamp utilizing discharge generated by the application of a high-frequency voltage of 50 Hz to several MHz via dielectrics (dielectric barrier discharge) as described in Kogelschatz, Pure & Appl. Chem. Vol. 62, No. 9, 1990, pp. 1667 to 1674.

The excimer lamp 30 preferably has large radiation intensity in a wavelength region shorter than 200 nm since the ozone generating wavelength is not more than 200 nm.

As a preferred specific example of the excimer lamp 30, may be mentioned a xenon excimer lamp with a center wavelength of 172 nm.

Figure 2:
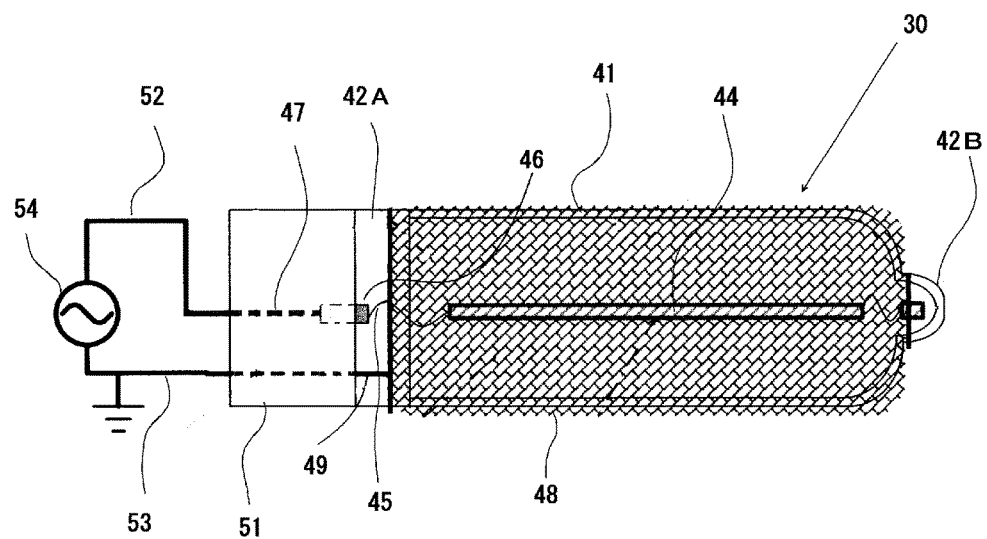
FIG. 2 is an explanatory view illustrating a configuration example of an excimer lamp that constitutes the ozone generator of FIG. 1 together with a base member and a high-frequency power source.

As shown in FIG. 2, the excimer lamp 30 is constituted by an ultraviolet transmitting material such as quartz, for example, and includes a right cylindrical arc tube 41 sealed at one end (the right end in FIG. 2) and having a flat sealing part 42A formed by pinch sealing at the other end (the left end in FIG. 2). In the arc tube 41, a rare gas such as a xenon gas is encapsulated and a coiled internal electrode 44 is disposed so as to extend along the tube axis of the arc tube 41. The internal electrode 44 is electrically connected to metal foil 46 buried in the sealing part 42A via an internal lead 45. One end of an internal electrode external lead 47 that protrudes outwardly from an outer end face of the sealing part 42A is electrically connected to the metal foil 46. The outer periphery of the arc tube 41 is provided with a net-like external electrode 48, and one end of an external electrode external lead 49 that extends along the sealing part 42A is electrically connected to the external electrode 48. An emission region is formed in a region where the internal electrode 44 and the external electrode 48 face each other via an internal space of the arc tube 41 and a tube wall of the arc tube 41. In this manner, a discharge space is formed in the arc tube 41.

A ceramic base member 51 is attached to the sealing part 42A of the excimer lamp 30. Feeder lines 52 and 53 are provided in this base member 51, and the other end of the external electrode external lead 49 and the other end of the internal electrode external lead 47 are connected to the feeder lines 52 and 53, respectively.

In the excimer lamp 30, the internal electrode 44 is connected to a high-frequency power source 54 via the internal lead 45, the metal foil 46, the internal electrode external lead 47, and the feeder line 52 of the base member 51. The external electrode 48 is grounded via the external electrode external lead 49 and the feeder line 53 of the base member 51.

In the example of FIG. 2, the arc tube 41 includes an exhaust tube remaining part 42B at one end.

The source gas contains oxygen.

As an example of the source gas, may be mentioned a gas constituting the external atmosphere of the ozone generator 10, i.e., air (ambient air).

In the example of FIG. 1, a gas constituting the external atmosphere (ambient air) is used as the source gas.

The source gas preferably has a relative humidity of not more than 30% RH, more preferably not more than 20% RH, inside the gas flow channel forming member 11 (gas flow channel), specifically, in the ozone generating part.

The source gas flowing through the gas flow channel that has a relative humidity of not more than 30% RH can generate ozone with higher efficiency as is apparent from an experimental example (specifically, Experimental Example 2) to be described later.

The source gas supply means 20 suitable in accordance with a type of a gas constituting the source gas and humidity conditions required for the source gas, for example, is employed.

Specifically, when the ambient air is employed as the source gas, the source gas supply means 20 capable of taking the ambient air from the outside of the ozone generator 10 and introducing the ambient air into the gas flow channel forming member 11 to be flowed therethrough is employed.

When a gas having a humidity lower than that of the ambient air (dry air) is employed as the source gas, the source gas supply means 20 capable of taking the ambient air from the outside of the ozone generator 10, dehumidifying the ambient air, and introducing the obtained dry air into the gas flow channel forming member to be flowed therethrough is employed.

In the example of FIG. 1, the source gas supply means 20 having a configuration in which a flexible duct 24 is attached to a gas inflow part 22A of a blower 21 is employed. The source gas supply means 20 is connected to the gas feed port 12A of the gas flow channel forming member 11 via a gas outflow part 22B of the blower 21, and one end 24A of the flexible duct 24 forms an intake port for taking the ambient air.

Supply conditions of the source gas by the source gas supply means 20 are appropriately determined in consideration of the inner diameter of the gas flow channel forming member 11, the outer diameter of the excimer lamp 30, etc., that allow the source gas to flow through the gas flow channel forming member 11 (gas flow channel) at a desired flow rate.

A flow rate of the source gas (hereinafter referred to also as a "flow rate of a light source supply gas") in the region where the excimer lamp 30 is disposed, specifically, the region where the emission region of the excimer lamp 30 is present (hereinafter referred to also as a "light source disposed region") inside the gas flow channel forming member 11 (gas flow channel) is set to be not lower than 0.1 m/s.

The flow rate of the light source supply gas as used herein refers to the flow rate of the source gas in the ring-shaped space partitioned by the inner periphery of the gas flow channel forming member 11 and the outer periphery of the excimer lamp 30. The flow rate of the light source supply gas is a value calculated by the following Mathematical Formula (1) wherein F [$m^3/s$] represents a gas flow volume in the gas flow channel and D [$m^2$] represents an area of the cross section of the light source disposed region perpendicular to the gas flowing direction. Note that the cross-sectional area D can be calculated by subtracting an area of the cross section of the excimer lamp 30 perpendicular to the gas flowing direction from an area of the cross section of the gas flow channel perpendicular to the gas flowing direction in the light source disposed region.

Flow rate of light source supply gas=$F/D$    Mathematical Formula (1):

When the flow rate of the light source supply gas is not lower than 0.1 m/s, ozone can be generated with high efficiency as is apparent from an experimental example (specifically, Experimental Example 1) to be described later.

The reason for this can be deduced as follows, although it is not necessarily clear.

Ozone is thermally decomposed, and the excimer lamp 30 has an increased temperature when lit. Thus, ozone generated in the ozone generating part could be thermally decomposed by heat from the excimer lamp 30. Therefore, if the source gas flows at a flow rate of the light source supply gas being not lower than 0.1 m/s, the generated ozone can be moved away from the ozone generating part before the occurrence of the thermal decomposition thereof by the flow of the source gas flowing along the excimer lamp 30. Furthermore, the flow of the source gas cools the excimer lamp 30, so that the occurrence of the thermal decomposition of ozone by the heat from the excimer lamp 30 is suppressed. Consequently, reduction in ozone yield due to the thermal decomposition of ozone by the heat from the excimer lamp 30 can be sufficiently suppressed.

As is apparent from the experimental example (specifically, Experimental Example 1) to be described later, the ozone generator 10 can achieve stable ozone generating efficiency when the flow rate of the light source supply gas is not lower than a certain value (specifically, not lower than 2 m/s, for example).

The flow rate of the light source supply gas can be adjusted, for example, by an input voltage to the blower 21 that constitutes the source gas supply means 20 or an area of the intake port (intake area) formed by the one end 24A of the flexible duct 24.

In the thus configured ozone generator 10, the source gas supply means 20 supplies, as the source gas, the gas constituting the external atmosphere (ambient air) to the inside of the gas flow channel forming member 11 (gas flow channel) via the gas feed port 12A. The source gas supplied into the gas flow channel forming member 11 flows through the source gas flowing part to reach the ozone generating part. In the ozone generating part, the source gas flowing toward the gas discharge port 12B is irradiated with light (ultraviolet light) from the excimer lamp 30. This causes oxygen in the source gas to absorb the ultraviolet light, thereby causing an ozone generating reaction to generate ozone. The ozone-containing gas containing the ozone generated by irradiating the source gas with ultraviolet light as just described flows through the ozone-containing gas flowing part to be discharged to the outside of the ozone generator 10 from the gas discharge port 12B of the gas flow channel forming member 11.

As described, the excimer lamp 30 that emits ultraviolet light with a wavelength of not more than 200 nm is employed as an ultraviolet light source in the ozone generator 10. Consequently, light (ultraviolet light) from the ultraviolet light source contains no light with the ozone decomposition wavelength (254 nm). Thus, no generated ozone is decomposed as a result of being irradiated with light (ultraviolet light) from the ultraviolet light source.

Moreover, since the excimer lamp 30 is disposed in the gas flow channel and the flow rate of the light source supply gas is set to be not lower than 0.1 m/s, reduction in ozone yield can be sufficiently suppressed. The reason for this can be deduced that the thermal decomposition of the generated ozone can be suppressed by the action of the flowing source gas as mentioned above.

Therefore, the ozone generator 10 can generate ozone with high efficiency.

Moreover, since the excimer lamp 30 is disposed along the gas flowing direction of the gas flow channel in the ozone generator 10, ozone can be generated with higher efficiency.

Moreover, by setting the relative humidity of the source gas flowing through the gas flow channel to be not more than 30% RH in the ozone generator 10, ozone can be generated with higher efficiency.

In the ozone generator 10, the ozone concentration of the ozone-containing gas to be discharged to the outside can be easily controlled by adjusting, for example, the supply conditions of the source gas and the shape of the gas flow channel (specifically, the inner diameter and the whole length of the gas flow channel forming member 11, the outer diameter and the whole length of the excimer lamp 30, and an electrical input to the excimer lamp 30, for example).

Thus, the ozone generator 10 can set the ozone concentration of the ozone-containing gas to be discharged to the outside to a concentration that leads to no negative effects on the human body, specifically, a concentration of not more than 50 ppm. Consequently, the ozone generator 10 can be suitably used as a sterilization and deodorization device for residence space. The sterilization and deodorization device for residence space that employs the ozone generator 10 can sterilize and deodorize the atmosphere of residence space with high efficiency.

While the ozone generator of the present invention has been specifically described above, the present invention is not limited to the above example. Various modifications can be made thereto.

For example, while the rod-shaped excimer lamp that constitutes the ultraviolet light source is preferably disposed along the flowing direction of the source gas from the viewpoint of the ozone generating efficiency as is apparent from the experimental example (specifically, Experimental Example 1) to be described later, the excimer lamp may be disposed perpendicular to the flowing direction of the source gas (see FIGS. 6 and 7).

In the ozone generator in which the excimer lamp is disposed perpendicular to the flowing direction of the source gas, the excimer lamp is disposed in such a way that the whole emission region is positioned inside the gas flow channel forming member (gas flow channel). As long as the emission region of the excimer lamp is positioned inside the gas flow channel forming member, the other portion thereof (specifically, both ends thereof, for example) may be positioned outside the gas flow channel forming member.

Experimental examples of the present invention will be described below.

Experimental Example 1

In Experimental Example 1, a relationship between a flow rate of a source gas (a flow rate of a light source supply gas) and an ozone yield (an ozone concentration in an obtained ozone-containing gas) and a relationship between a disposed state (orientation in a gas flow channel) of an ultraviolet light source (excimer lamp) and an ozone yield (an ozone concentration in an obtained ozone-containing gas) were confirmed.

Figure 3:
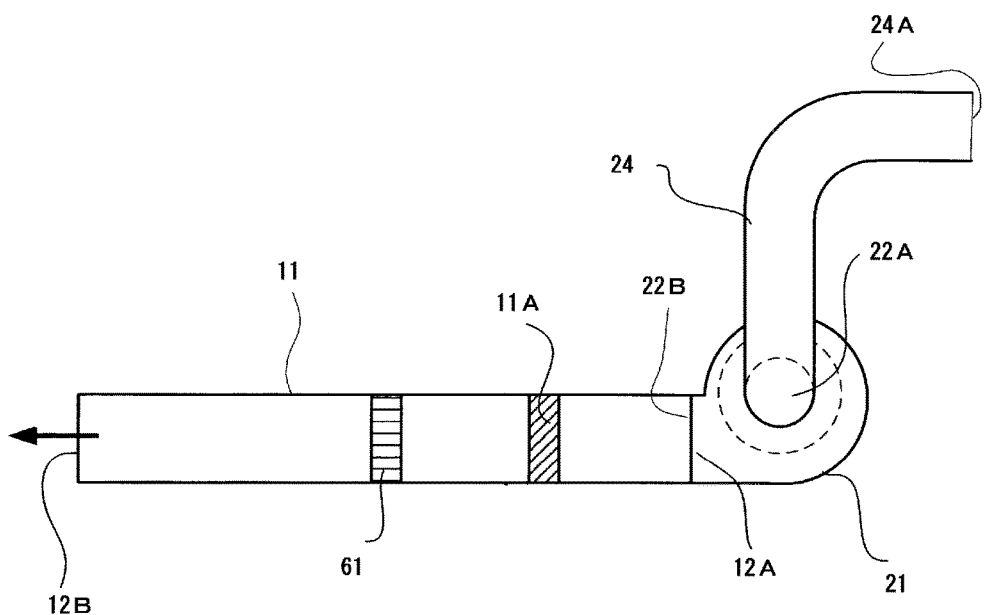
FIG. 3 is an explanatory view illustrating a schematic configuration of two ozone generators used in Experimental Example 1.
Figure 4:
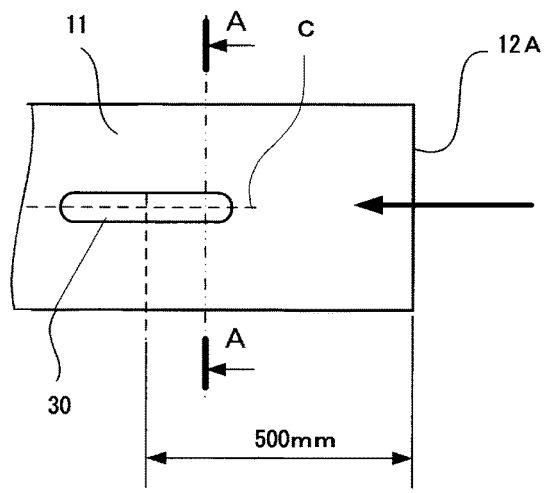
FIG. 4 is an explanatory view illustrating a main part (lamp disposed part) of the configuration of one of the ozone generators used in Experimental Example 1.
Figure 5:
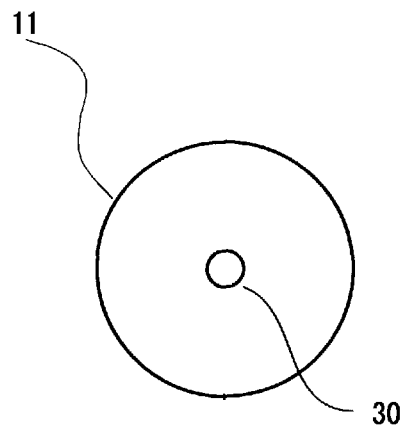
FIG. 5 is a cross-sectional view taken along line A-A in FIG. 4.

An experimental ozone generator (hereinafter referred to also as an "ozone generator (A)") as shown in FIGS. 3 to 5 was produced in compliance with "Testing and inspection methods for blowers" of JIS B 8330.

As shown in FIG. 3, the ozone generator (A) includes a gas flow channel forming member 11 having a right cylindrical shape. The gas flow channel forming member 11 has a gas feed port 12A at one end and a gas discharge port 12B at the other end. Source gas supply means 20 having a configuration in which a flexible duct 24 is attached to a gas inflow part 22A of a blower 21 is connected to the gas feed port 12A via a gas outflow part 22B of the blower 21. In a lamp disposed part 11A of the gas flow channel forming member 11, an excimer lamp 30 having the configuration of FIG. 2 is disposed in such a manner that the whole emission region is positioned inside the gas flow channel forming member 11 and a tube axis (the central axis of the lamp) C approximately coincides with a tube axis of the gas flow channel forming member 11 as shown in FIGS. 4 and 5. That is, the excimer lamp 30 is disposed so as to extend in a direction along the flowing direction of the source gas in the gas flow channel.

In FIGS. 3 and 4, the flowing direction of the gas in the ozone generator (A) is indicated by the arrow.

In the ozone generator (A), the gas flow channel forming member 11 has a whole length of 2 m obtained by connecting two straight tubes, made of a vinyl chloride resin and each having an inner diameter of 100 mm and a whole length of 1 m. A rectifier grid 61 with a thickness of 30 mm and a grid shape (grid dimensions: 10 mm×10 mm) is disposed at a seam between the two straight tubes. The excimer lamp 30 was disposed around a position spaced apart from the gas feed port 12A by 500 mm in the gas flow channel forming member 11 (see FIG. 4).

In the source gas supply means 20, "DC blower: MBD12-24" (manufactured by ORIENTAL MOTOR Co., Ltd.) was employed as the blower 21, and the flexible duct 24 made of aluminum and having an inner diameter of 100 mm and a whole length of 2 m was employed.

A xenon excimer lamp having an emission length of 90 mm and including an exhaust tube remaining part 42B (see FIG. 2) with a protruded height of 5 mm was employed as the excimer lamp 30. A base member 51 (see FIG. 2) with a whole length (the length in the tube axis direction of the excimer lamp 30) of 10 mm was attached to the excimer lamp 30.

Figure 6:
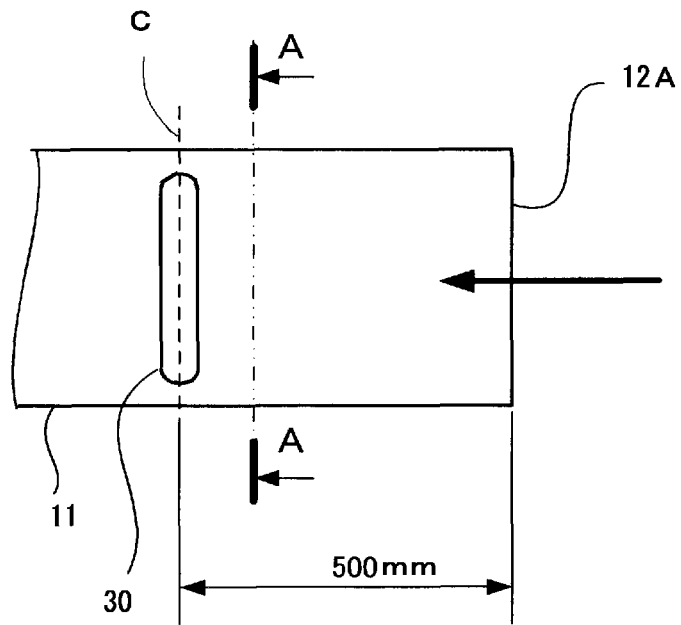
FIG. 6 is an explanatory view illustrating a main part (lamp disposed part) of the configuration of the other one of the ozone generators used in Experimental Example 1.
Figure 7:
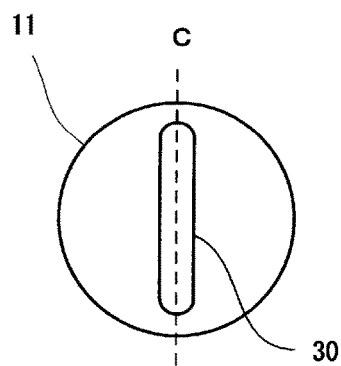
FIG. 7 is a cross-sectional view taken along line A-A in FIG. 6.

An experimental ozone generator (hereinafter referred to also as an "ozone generator (B)") having the same configuration as the ozone generator (A) except that the excimer lamp 30 is disposed in such a manner that the tube axis (the central axis of the lamp) C extends in a direction perpendicular to the tube axis of the gas flow channel forming member 11 (direction perpendicular to the flowing direction of the source gas in the gas flow channel) in the ozone generator (A) as shown in FIGS. 6 and 7 was produced.

In the ozone generator (B), the excimer lamp 30 is provided in such a manner that the excimer lamp 30 passes through the gas flow channel forming member 11 in a radial direction thereof at a position spaced apart from the gas feed port 12A by 500 mm, the emission region of the excimer lamp 30 is positioned inside the gas flow channel forming member 11, and part of the base member 51 (see FIG. 2) and the exhaust tube remaining part 42B (see FIG. 2) protrude from the outer periphery of the gas flow channel forming member 11. The protruded portions of the base member 51 and the exhaust tube remaining part 42B are sealed with an aluminum tape.

In FIG. 6, the flowing direction of the gas in the ozone generator (B) is indicated by the arrow.

Figure 8:
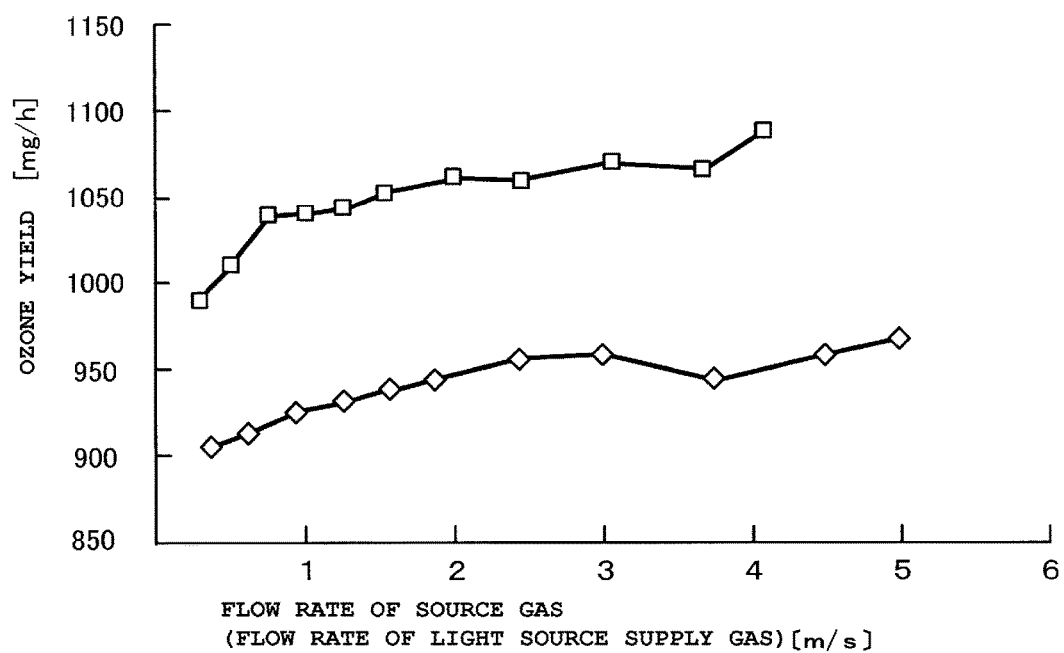
FIG. 8 is a graph showing a relationship between a flow rate of a source gas in a region where an excimer lamp is disposed inside a gas flow channel forming member and an ozone yield that is obtained in Experimental Example 1.
Figure 9:
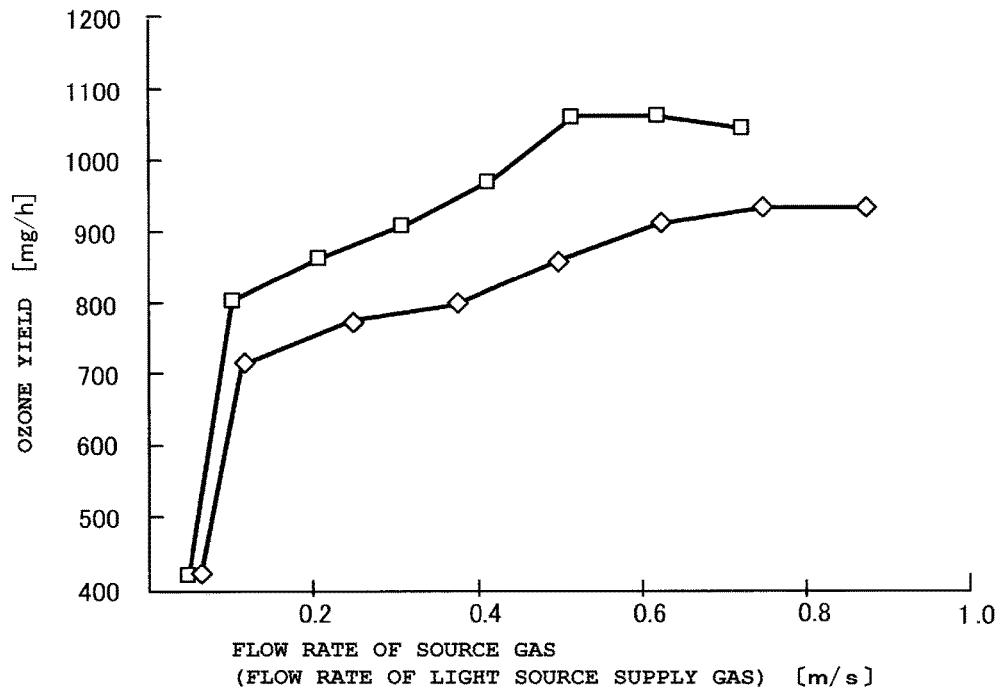
FIG. 9 is a graph showing, in detail, a region having low flow rates of the source gas in the region where the excimer lamp is disposed inside the gas flow channel forming member in the graph of FIG. 8.

A source gas comprising a gas that constitutes the external atmosphere (ambient air) was supplied to each of the produced ozone generator (A) and ozone generator (B) at various flow rates (flow rates of the light source supply gas). Here, the flow rate of the source gas (the flow rate of the light source supply gas) was adjusted by shielding part of an intake port formed by the one end 24A of the flexible duct 24 or by adjusting an input voltage to the blower 21. Thereafter, it was confirmed that the humidity (relative humidity) of the flowing source gas was 26% RH in a region inside the gas flow channel forming member 11 (gas flow channel) where the excimer lamp 30 was disposed (a light source disposed region). Immediately after that, the excimer lamp 30 was lit and an ozone yield was measured in the light source disposed region. The results are shown in FIGS. 8 and 9. In FIGS. 8 and 9, the result related to the ozone generator (A) is indicated by a square plot (□), and the result related to the ozone generator (B) is indicated by a rhombic plot (◇).

Figure 10:
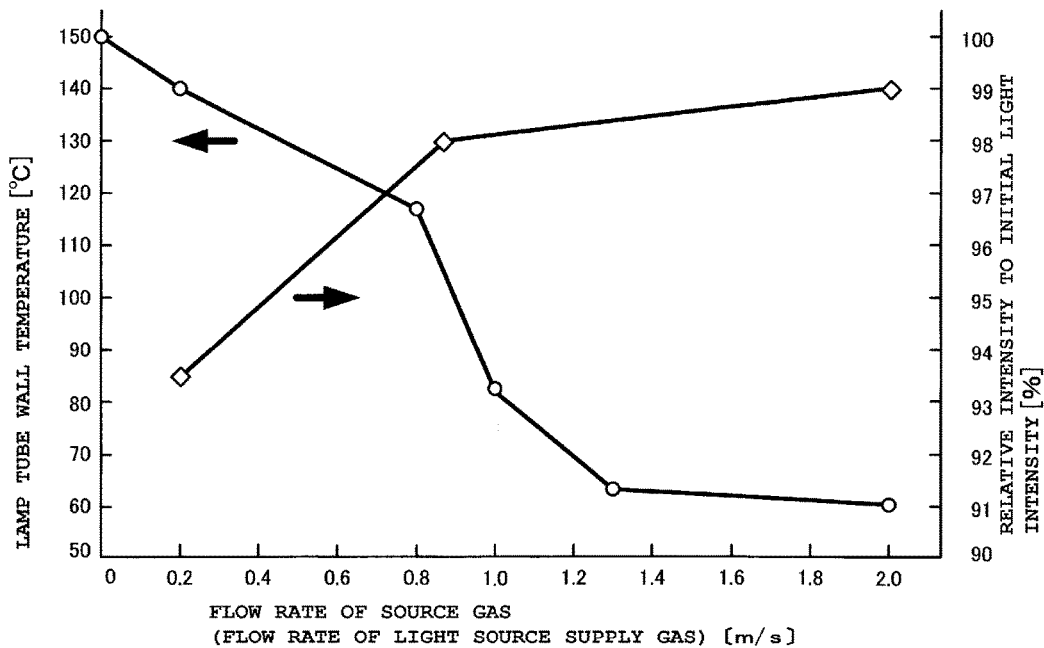
FIG. 10 shows a graph showing a relationship between a flow rate of the source gas in the region where the excimer lamp is disposed inside the gas flow channel forming member and a temperature of a tube wall of an arc tube and a graph showing a relationship between the flow rate of the source gas and light intensity (relative intensity to initial light intensity) of light emitted from the excimer lamp that are obtained in Experimental Example 1.

Moreover, in the ozone generator (A), the temperature of a tube wall of an arc tube 41 (see FIG. 2) (lamp tube wall temperature) in the excimer lamp 30 was measured while the excimer lamp 30 was lit, and light intensity of light emitted from the excimer lamp 30 was measured. Relative intensity (relative intensity to initial light intensity) wherein light intensity (initial light intensity) when the tube wall of the arc tube 41 had a temperature of 40° C. was defined as 100% was calculated. The results are shown in FIG. 10. In FIG. 10, the result related to the lamp tube wall temperature is indicated by a circular plot (○), and the result related to the relative intensity to the initial light intensity is indicated by a rhombic plot (◇).

It was confirmed from the results of Experimental Example 1 that, when the excimer lamp that emits ultraviolet light with a wavelength of not more than 200 nm is employed as an ultraviolet light source, ozone can be generated with high efficiency by setting the flow rate of the source gas (the flow rate of the light source supply gas) in the region where the excimer lamp (ultraviolet light source) is disposed (light source disposed region) in the gas flow channel to be not lower than 0.1 m/s. It was further confirmed that stable ozone generating efficiency can be obtained when the flow rate of the light source supply gas is not lower than a certain value (specifically, not lower than 2 m/s).

When the rod-shaped excimer lamp is employed as an ultraviolet light source, it was confirmed that ozone can be generated with higher efficiency by disposing the excimer lamp along the flowing direction of the source gas in the gas flow channel.

More specifically, as is apparent from FIG. 8, in any of the ozone generator (A) and the ozone generator (B), the ozone yield gradually increases until the flow rate of the light source supply gas reaches 2.0 m/s. When the flow rate of the light source supply gas exceeds 2.0 m/s, however, the ozone yield becomes stable at a substantially constant value. As is apparent from FIG. 9, whereas the ozone yield is about 420 mg/h at a flow rate of the light source supply gas of 0.05 m/s, the ozone yield at a flow rate of the light source supply gas of about 0.1 m/s drastically increases to 810 mg/h in the ozone generator (A) and to 710 mg/h in the ozone generator (B).

As is apparent from FIGS. 8 and 9, comparison between the ozone generator (A) and the ozone generator (B) shows that the ozone generator (A) has a larger ozone yield than the ozone generator (B).

The reason for this can be deduced as follows based on FIG. 10.

As mentioned above, in the excimer lamp, the light intensity of emitted light decreases as the temperature of the tube wall of the arc tube increases. As is apparent from FIG. 10, until the flow rate of the light source supply gas reaches 1 m/s, the temperature of the tube wall of the arc tube decreases and the light intensity of light emitted from the excimer lamp gradually increases as the flow rate increases. When the flow rate of the source gas exceeds 1 m/s, on the other hand, decrease in the temperature of the tube wall of the arc tube gradually diminishes and the light intensity of light emitted from the excimer lamp gradually becomes stable. When the flow rate of the light source supply gas is 2 m/s, the temperature of the tube wall of the arc tube is settled at 61° C. and the intensity (relative intensity) of light emitted from the excimer lamp is settled at 99%. Here, when the flow rate of the light source supply gas exceeded 2 m/s, the temperature of the tube wall of the excimer lamp and the light intensity (relative intensity) of light emitted from the excimer lamp were almost the same as those when the flow rate of the light source supply gas was 2 m/s, although not shown in FIG. 10.

From the above, the reason why ozone can be generated with high efficiency by setting the flow rate of the light source supply gas to be not lower than 0.1 m/s is as mentioned previously. That is, it can be deduced that the reason is because the flow of the source gas can move the generated ozone away from the vicinity of the excimer lamp before the thermal decomposition of the generated ozone occurs and can cool the excimer lamp, so that reduction in ozone yield due to the thermal decomposition of ozone by heat from the excimer lamp can be sufficiently suppressed. When the flow rate of the light source supply gas is lower than 0.1 m/s, on the other hand, it can be deduced that the ozone yield significantly reduces since the stagnation of ozone in the vicinity of the excimer lamp becomes prominent and so the effect of the thermal decomposition of ozone due to the heat from the excimer lamp increases.

It can be deduced that the reason why stable ozone generating efficiency is obtained when the flow rate of the light source supply gas is not lower than a certain value (specifically, not lower than 2 m/s) is because the light intensity of light emitted from the excimer lamp is stabilized at a certain value.

It can be deduced that the reason why ozone can be generated with higher efficiency by disposing the excimer lamp along the flowing direction of the source gas in the gas flow channel is because the source gas is less likely to stagnate as compared to a case where the excimer lamp is disposed perpendicular to the flowing direction of the source gas in the gas flow channel and so the effect of the thermal decomposition of ozone by the heat from the excimer lamp reduces.

Experimental Example 2

In Experimental Example 2, a relationship between a humidity (relative humidity) of a source gas and an ozone yield (an ozone concentration in an obtained ozone-containing gas) was confirmed.

Figure 11:
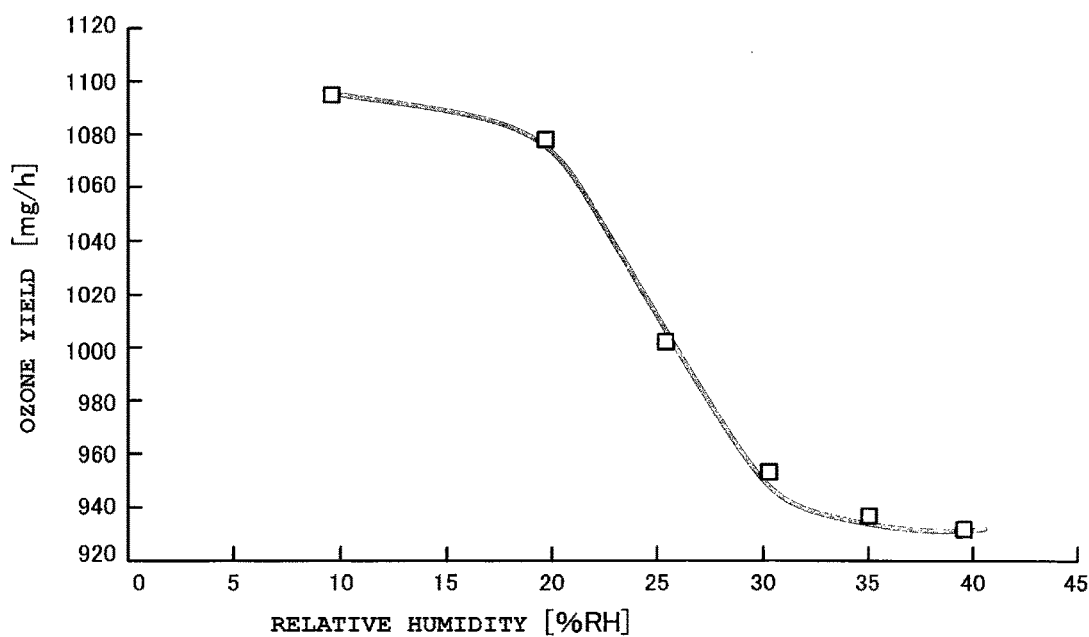
FIG. 11 is a graph showing a relationship between a relative humidity of a source gas flowing through the gas flow channel forming member and an ozone yield that is obtained in Experimental Example 2.

Using the ozone generator (A) produced in Experimental Example 1, air, specifically, dry air, a gas that constitutes the external atmosphere (ambient air), and an adjusted gas obtained by mixing mist from an ultrasonic humidifier into dry air or the ambient air as needed, at various humidities (relative humidities) was supplied so that the flow rate of the source gas (the flow rate of the light source supply gas) in the region where the excimer lamp was disposed (the light source disposed region) inside the gas flow channel forming member (gas flow channel) had a value of 0.9 m/s, and ozone yields in that region were measured. The result is shown in FIG. 11.

It was confirmed from the result of Experimental Example 2 that ozone can be generated with high efficiency when the source gas has a relative humidity of not more than 30% RH and ozone can be generated with higher efficiency especially when the source gas has a relative humidity of not more than 20% RH.

The reason for this can be deduced as follows.

In general, water has a larger absorption coefficient with respect to ultraviolet light with a wavelength of not more than 200 nm than oxygen. Thus, in the source gas, an amount of ultraviolet light absorbed by moisture (water) increases with an increase in humidity. An amount of ultraviolet light absorbed by oxygen decreases accordingly, thus resulting in reduction in ozone yield. Oxygen that has absorbed ultraviolet light is photodegraded into an oxygen atom. The oxygen atom reacts (binds) with oxygen to generate ozone. The oxygen atom generated by the photodegradation, on the other hand, also reacts with moisture (water molecule) to generate a hydroxyl radical (OH radical). When the source gas has high humidity, the reaction between an oxygen atom generated by the photodegradation of oxygen and moisture (hydroxyl radical generating reaction) dominates over the reaction between an oxygen atom and oxygen (ozone generating reaction), thus resulting in reduction in ozone yield. Furthermore, hydroxyl radicals involve in the decomposition of ozone. Therefore, by using a low-humidity source gas with a relative humidity of not more than 30% RH, reduction in ozone yield due to the moisture contained in the source gas can be sufficiently suppressed.

REFERENCE SIGNS LIST 10 ozone generator
11 gas flow channel forming member
11A lamp disposed part
12A gas feed port
12B gas discharge port
20 source gas supply means
21 blower
22A gas inflow part
22B gas outflow part
24 flexible duct 24A one end
30 excimer lamp
41 arc tube
42A sealing part
42B exhaust tube remaining part
44 internal electrode
45 internal lead
46 metal foil
47 internal electrode external lead
48 external electrode
49 external electrode external lead
51 base member
52, 53 feeder line
54 high-frequency power source
61 rectifier grid

The invention claimed is:

1. An ozone generator comprising:
source gas supply means for supplying a source gas containing oxygen into a gas flow channel forming member; and an ultraviolet light source for emitting ultraviolet light, the ultraviolet light source being disposed in the gas flow channel forming member, the ozone generator irradiating the source gas with the ultraviolet light from the ultraviolet light source to cause the oxygen in the source gas to absorb the ultraviolet light and thereby generate ozone, wherein
the gas flow channel forming member has a gas feed port at one end and a gas discharge port at the other end, and forming a gas flow channel through which the source gas from the source gas supply means flows,
the ultraviolet light source comprises an excimer lamp for emitting ultraviolet light with a wavelength of not more than 200 nm and irradiates the source gas flowing through the gas flow channel with the ultraviolet light, and
a flow rate of the source gas in a region where the ultraviolet light source is disposed in the gas flow channel is not lower than 0.1 m/s.

2. The ozone generator according to claim 1, wherein the excimer lamp that constitutes the ultraviolet light source has a rod shape, and the excimer lamp is disposed along a gas flowing direction in the gas flow channel.

3. The ozone generator according to claim 2, wherein an ozone concentration in an ozone-containing gas discharged to the outside is not more than 50 ppm, and the ozone generator is used as a sterilization and deodorization device for residence space.

4. The ozone generator according to claim 1, wherein the source gas flowing through the gas flow channel has a relative humidity of not more than 30% RH.

5. The ozone generator according to claim 4, wherein an ozone concentration in an ozone-containing gas discharged to the outside is not more than 50 ppm, and the ozone generator is used as a sterilization and deodorization device for residence space.

6. The ozone generator according to claim 1, wherein an ozone concentration in an ozone-containing gas discharged to the outside is not more than 50 ppm, and the ozone generator is used as a sterilization and deodorization device for residence space.

* * * * *